(12) United States Patent
Imamoto et al.

(10) Patent No.: US 6,251,861 B1
(45) Date of Patent: *Jun. 26, 2001

(54) TREATMENT OF CEREBRAL INFARCTION USING CYCLIC HEXAPEPTIDES

(75) Inventors: Tetsuji Imamoto, Kitakatsuragi-gun; Yasutaka Nagisa, Osaka, both of (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/881,878

(22) Filed: Jun. 24, 1997

(30) Foreign Application Priority Data

Jun. 27, 1996 (JP) ................................ 8-167507

(51) Int. Cl.⁷ ........................ A61K 38/12; A61K 38/08
(52) U.S. Cl. .................... 514/11; 514/9; 514/17; 530/317
(58) Field of Search ................ 530/317; 514/9–11, 514/17

(56) References Cited

U.S. PATENT DOCUMENTS

| | | | |
|---|---|---|---|
| 5,616,684 | * | 4/1997 | Wakimasu et al. . |
| 5,714,479 | * | 2/1998 | Ishikawa et al. . |
| 5,731,321 | * | 3/1998 | Mederski et al. . |
| 5,753,619 | * | 5/1998 | Watanabe et al. . |
| 5,883,075 | * | 3/1999 | Wakimasu et al. . |
| 5,948,754 | * | 9/1999 | Wakimasu et al. . |

FOREIGN PATENT DOCUMENTS

| | | |
|---|---|---|
| 0 357 510 A1 | 8/1989 | (EP) . |
| 0 528 312 | 2/1993 | (EP) . |
| 0 647 449 A1 | 6/1994 | (EP) . |
| 0 626 174 | 11/1994 | (EP) . |
| 0 655 463 | 5/1995 | (EP) . |
| 0 714 909 | 6/1996 | (EP) . |
| WO 93/17701 | 9/1993 | (WO) . |

OTHER PUBLICATIONS

Copy of European Search Report.
Zavi et al. Stroke, vol. 23, No. 7, 1014–1016 (1992).
C.O.E. International Symposium The 10th Japan Symposium on ANP Nov. 18–20, 1995, p. 42.

* cited by examiner

*Primary Examiner*—Marianne P. Allen
(74) *Attorney, Agent, or Firm*—David G. Conlin; Dike, Bronstein, Roberts & Cushman; Intellectual Property Group of Edwards & Angell, LLP

(57) ABSTRACT

A pharmaceutical composition comprising a compound having anti-endothelin activity is useful for the prophylaxis or treatment of cerebral infarction.

3 Claims, No Drawings

TREATMENT OF CEREBRAL INFARCTION USING CYCLIC HEXAPEPTIDES

This application is based on application No. 167507/1996 filed in Japan, the content of which is incorporated hereinto by reference.

TECHNICAL FIELD

The present invention relates to a pharmaceutical composition for prophylaxis or treatment of cerebral infarction which comprises a compound having a specific chemical structure and anti-endothelin activity.

BACKGROUND ART

Endothelin (ET) is a vasoconstrictor peptide composed of 21 amino acid residues, which was first isolated from a culture supernatant of porcine aortic endothelial cells and characterized (Yanagizawa et al., Nature, 332, 411–415, 1988). Subsequent research suggested that endothelin occurs in at least 3 isoforms (ET-1, ET-2 and ET-3), and two endothelin receptors, $ET_A$ (being concerned with only action of vasoconstriction) and $ET_B$ (being concerned with mainly action of vasodilation), have been identified.

Since the discovery of endothelin, searches for anti-endothelin compounds have been energetically undertaken to develop therapeutic drugs for diseases pathologically associated with endothelin. Results of such exploratory endeavors have been reported in EP-A-552,489, EP-A-528,312, EP-A-499,266, WO 91/13089, EP-A-436,189, EP-A-457,195, EP-A-510,526, WO 92/12991, EP-A-496,452, EP-A-526,708, EP-A-460,679, WO 92/20706, among other reports. The compounds described in the above reports are suggested to be effective as anti-hypertensive agents, therapeutic drugs for cardiovascular/cerebrovascular diseases (such as myocardial infarction), therapeutic drugs for diseases of the kidney, antiasthmatic agents, antiinflammatory agents, and/or antiarthritic agents but there is no specific description about their application as a therapeutic or prophylactic drug for cerebral infarction. On the other hand, EP-A-655,463 describes that a compound which exhibits excellent antagonistic action against endothelin B receptors is useful for diseases caused by endothelin, such as hypertension, cerebral infarction, etc.

In view of the above state of the art, the inventors of the present invention investigated agents of use for the clinically beneficial prevention or treatment of cerebral infarction and firstly found surprisingly that anti-endothelin compounds having specific chemical structure are effective for the purpose, based on concrete data. They accordingly have perfected the present invention.

SUMMARY OF THE INVENTION

The present invention relates to a pharmaceutical composition for the prophylaxis and/or therapeutic efficacy of cerebral infarction which comprises a compound having a specific chemical structure and anti-endothelin activity.

DETAILED EXPLANATION OF THE INVENTION

The present invention relates to:

(1) a pharmaceutical composition for the prophylaxis or treatment of cerebral infarction which comprises a compound having anti-endothelin activity;

(2) the pharmaceutical composition according to (1) wherein the anti-endothelin activity is endothelin receptor antagonistic activity;

(3) the pharmaceutical composition according to (1) wherein the compound having anti-endothelin activity is a peptide compound;

(4) the pharmaceutical composition according to (1) wherein the compound having anti-endothelin activity is a cyclic hexapeptide of the formula:

[I]

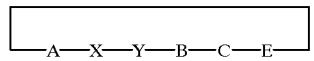

wherein X and Y each represents an α-amino acid residue having D-, L- or DL-form; A represents a D-acidic α-amino acid residue; B represents a D- or L-neutral-α-amino acid residue; C represents a L-α-amino acid residue; E represents a D-α-amino acid residue having an aromatic ring group, or an ester thereof, or a salt thereof;

(5) the pharmaceutical composition according to (3) wherein the cyclic hexapeptide is a compound of the formula Cyclo[-D-Asp-Asp(R1)-Asp-D-Thg(2)-Leu-D-Trp-]

wherein Asp(R1) is an aspartic acid β-4-phenylpiperazine amide residue and Thg(2) is a 2-thienylglycine residue or a salt thereof; and so forth.

The anti-endothelin compound that can be used in the present invention is any peptide compound that can be administered as an anti-endothelin drug and is capable of accomplishing the object of the invention.

Among the preferred examples of such anti-endothelin compound are peptides of the formula [I] and their salts. Such salts are pharmaceutically acceptable salts such as salts with inorganic bases, salts with organic bases, salts with inorganic acids, salts with organic acids, and salts with basic or acidic amino acids.

Among preferred salts with inorganic bases are salts with alkali metals such as sodium, potassium, etc., salts with alkaline earth metals such as calcium, magnesium, etc., aluminum salts, and ammonium salts.

Among preferred salts with organic acids are salts with trimethylamine, triethylamine, pyridine, picoline, ethanolamine, diethanolamine, triethanolamine, dicyclohexylamine, and N,N'-dibenzylethylenediamine.

Among preferred salts with inorganic acids are salts with hydrochloric acid, hydrobromic acid, nitric acid, sulfuric acid, and phosphoric acid.

Among preferred salts with organic acids are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

Among preferred salts with basic amino acids are salts with arginine, lysine, and ornithine.

Among preferred salts with acidic amino acids are salts with aspartic acid and glutamic acid.

Referring to the formula [I], the precursor amino acid for the α-amino acid residue for X and Y can be any α-amino acid, thus including alanine, arginine, asparagine, aspartic acid, cysteine, glutamine, glutamic acid, 2-aminomalonic acid, 2-aminoadipic acid, glycine, histidine, isoleucine, leucine, lysine, ornithine, 2,4-diaminobutyric acid, methionine, phenylalanine, proline, 4-hydroxyproline, thioproline, azetidine-2-carboxylic acid, pipecolic acid (piperidine-2-carboxylic acid), indoline-2-carboxylic acid, tetrahydroisoquinoline-3-carboxylic acid, serine, thereonine, tryptophan, 5-methyltryptophan, tyrosine, valine, alloisoleucine, norvaline, norleucine, tert-leucine, γ-methylleucine, phenylglycine, 2-aminobutyric acid, cysteic acid, homocysteic acid, 1-naphthylalanine, 2-naphthylalanine, 2-thienylglycine, 3-thienylglycine, 3-benzothienylalanine, 4-biphenylalanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, and 1-aminocycloheptane-1-carboxylic acid.

Where such α-amino acids have functional groups such as hydroxy, thiol, amino, imino, carboxy, etc., such functional groups may be substituted by suitable substituent groups.

The substituted hydroxy, for instance, includes $C_{1-6}$ alkanoyloxy (e.g. formyloxy, acetoxy, propionyloxy, etc.), $C_{4-9}$ alicycle-carbonyloxy (e.g. cyclopentanecarbonyloxy, cyclohexanecarbonyloxy, etc.), $C_{7-15}$ arylcarbonyloxy (e.g. benzoyloxy, 4-methylbenzoyloxy, etc.), $C_{8-16}$ aralkylcarbonyloxy (e.g. phenylacetoxy, 2-phenylpropionyloxy, 3-phenylpropionyloxy, diphenylacetoxy, etc.), aromatic heterocycle-alkylcarbonyloxy (e.g. indol-2-ylacetoxy, indol-3-ylacetoxy, etc.), $C_{1-6}$ alkoxy (e.g. methoxy, ethoxy, n-propoxy, tert-butoxy, etc.), $C_{3-8}$ cycloalkoxy (e.g. cyclopentyloxy, cyclohexyloxy, etc.), $C_{6-12}$ aryloxy (e.g. phenyloxy, 4-methylphenyloxy, etc.), and $C_{7-15}$ aralkyloxy (e.g. benzyloxy, phenethyloxy, diphenylmethoxy, etc.), among others. The α-amino acid containing such a substituted hydroxy group includes but is not limited to O-acetylserine, O-acetylthreonine, 4-acetoxyproline, O-benzoylserine, O-benzoylthreonine, 4-benzoyloxyproline, O-phenylacetylserine, O-phenylacetylthreonine, 4-phenylacetoxyproline, O-ethylserine, O-ethylthreonine, 4-ethoxyproline, O-cyclohexylserine, O-cyclohexylthreonine, 4-cyclohexyloxyproline, O-phenylserine, O-phenylthreonine, 4-phenoxyproline, O-benzylserine, O-benzylthreonine, 4-benzyloxyproline, O-diphenylmethylserine, O-diphenylmethylthreonine, and 4-diphenylmethoxyproline.

The substituted thiol includes, for example, $C_{1-6}$ alkanoylthio (e.g. formylthio, acetylthio, propionylthio, etc.), $C_{4-9}$ alicycle-carbonylthio (e.g. cyclopentanecarbonylthio, cyclohexanecarbonylthio, etc.), $C_{7-15}$ arylcarbonylthio (e.g. benzoylthio, 4-methylbenzoylthio, etc.), $C_{8-16}$ aralkylcarbonylthio (e.g. phenylacetylthio, 2-phenylpropionylthio, 3-phenylpropionylthio, diphenylacetylthio, etc.), $C_{1-6}$ alkylthio (e.g. methylthio, ethylthio, n-propylthio, tert-butylthio, etc.), $C_{3-8}$ cycloalkylthio (e.g. cyclopentylthio, cyclohexylthio, etc.), $C_{6-12}$ arylthio (e.g. phenylthio, 4-methylphenylthio, etc.), $C_{7-15}$ aralkylthio (e.g. benzylthio, phenethylthio, diphenylmethylthio, etc.). The α-amino acid having such a substituted thiol group includes but is not limited to S-acetylcysteine, S-benzoylcysteine, S-phenylacetylcysteine, S-ethylcysteine, S-cyclohexylcysteine, S-phenylcysteine, and S-benzylcysteine.

The substituted amino includes, for example, $C_{1-6}$ alkylamino (e.g. N-methylamino, N-ethylamino, N-tert-butylamino, etc.), $C_{3-8}$ cycloalkylamino (e.g. N-cyclopentylamino, N-cyclohexylamino, etc.), $C_{6-12}$ arylamino (e.g. N-phenylamino, N-{4-methylphenyl}amino, etc.), $C_{7-15}$ aralkylamino (e.g. N-benzylamino, N-phenethylamino, N-{2-chlorobenzyl}amino, N-{3-chlorobenzyl}amino, N-{4-chlorobenzyl}amino, N-{2-methylbenzyl}amino, N-{3-methylbenzyl}amino, N-{4-methylbenzyl}amino, N-{2-methoxybenzyl}amino, N-{3-methoxybenzyl}amino, N-{4-methoxybenzyl}amino, etc.), aromatic heterocycle-$C_{1-6}$ alkylamino (e.g. 2-furylmethylamino, 3-furylmethylamino, 2-thienylmethylamino, 3-thienylmethylamino, indol-2-ylmethylamino, indol-3-ylmethylamino, etc.). The substituted amido group includes, for example, $C_{1-6}$ aliphatic acylamido (e.g. formamido, acetamido, propionamido, etc.), $C_{4-9}$ alicyclic acylamido (e.g. cyclopentanecarbonylamido, cyclohexanecarbonylamido, etc.), $C_{7-15}$ aryl acylamido (e.g. benzamido, 4-methylbenzamido, etc.), $C_{8-16}$ aralkyl acylamido (e.g. phenylacetamido, 2-phenylpropionamido, 3-phenylpropionamido, diphenylacetamido, 1-naphthylacetamido, 2-naphthylacetamido, etc.), aromatic heterocycle-carboxamido (e.g. indol-2-ylcarboxamido, indol-3-ylcarboxamido, etc.), aromatic heterocyclealkylcarboxamido (e.g. indol-2-ylacetamido, indol-3-ylacetamido, etc.), sulfonylamido (e.g. benzenesulfonylamido, p-toluenesuflonylamido, 4-methoxy-2,3,6-trimethylbenzenesulfonylamido, etc.), etc.

The substituent group for the substituted imino includes the same $C_{1-6}$ alkyl, $C_{3-8}$ cycloalkyl, $C_{6-12}$ aryl, $C_{7-15}$ aralkyl and aromatic heterocycle-$C_{1-6}$ alkyl groups as mentioned for the substituted amino or amido.

The α-amino acid with substituted amino includes but is not limited to N-methylglycine (sarcosine), N-ethylglycine, N-methylleucine, N-ethylleucine, N-methylphenylalanine, N-ethylphenylalanine, N(α)-methyltryptophan, N(α)-ethyltryptophan, N-cyclopentylglycine, N-cyclohexylglycine, N-phenylglycine, N-phenylleucine, N-benzylglycine, N-benzylleucine, N(π)-benzylhistidine, N(τ)-benzylhistidine, N(π)-phenacylhistidine, N(π)-benzyloxymethylhistidine, $N^g$-benzenesulfonylarginine, $N^g$-p-toluenesulfonylarginine, $N^g$-(4-methoxy-2,3,6-trimethylbenzenesulfonyl)arginine, N(ε)-benzenesulfonyllysine, N(ε)-p-toluenesulfonyllysine, N(ε)-(4-methoxy-2,3,6-trimethylbenzenesulfonyl)lysine, $N^{in}$-methyltryptophan, $N^{in}$-ethyltryptophan, $N^{in}$-formyltryptophan, $N^{in}$-acetyltryptophan, N(ε)-benzyllysine, N(ε)-(2-furylmethyl)lysine, N(ε)-(2-thienylmethyl)lysine, N(ε)-(indol-3-ylmethyl)lysine, N(ε)-phenylacetyllysine, N(ε)-({2-furyl}acetyl)lysine, N(ε)-({2-thienyl}acetyl)lysine, N(ε)-({indol-3-yl}acetyl)lysine, N(ε)-benzoyllysine, N(ε)-(3-phenylpropionyl)lysine, N(δ)-benzylornithine, N(δ)-(2-furylmethyl)ornithine, N(δ)-(2-thienylmethyl)ornithine, N(δ)-(indol-3-ylmethyl)ornithine, N(δ)-benzoylornithine, N(δ)-phenylacetylornithine, N(δ)-(3-phenylpropionyl)ornithine, N(δ)-({2-methylphenyl}acetyl)ornithine, N(δ)-({3-methylphenyl}acetyl)ornithine, N(δ)-({4-methylphenyl}acetyl)ornithine, N(δ)-({2-chlorophenyl}acetyl)ornithine, N(δ)-({3-chlorophenyl}acetyl)ornithine, N(δ)-({4-chlorophenyl}acetyl)ornithine, N(δ)-({2-methoxyphenyl}acetyl)ornithine, N(δ)-({3-methoxyphenyl}acetyl)ornithine, N(δ)-({4-methoxyphenyl}acetyl)ornithine, N(δ)-(4-biphenylacetyl)ornithine, N(γ)-benzyl-2,4,-diaminobutyric acid, N(γ)-(2-furylmethyl)-2,4-diaminobutyric acid, N(γ)-(2-thienylmethyl)-2,4-diaminobutyric acid, N(γ)-(indol-3-ylmethyl)-2,4-diaminobutyric acid, N(γ)-benzoyl-2,4-diaminobutyric acid, N(γ)-phenylacetyl-2,4-diaminobutyric acid, N(γ)-(3-phenylpropionyl)-2,4-diaminobutyric acid, N(γ)-(2 furylacetyl)-2,4-diaminobutyric acid, N(γ)-(2-thienylacetyl)-2,4-diaminobutyric acid, and N(γ)-({indol-3-yl}acetyl)-2,4-diaminobutyric acid.

The substituted carboxy includes, for example, carbamoyl ($—CONH_2$), $C_{1-6}$ alkylcarbamoyl (e.g. methylcarbamoyl, ethylcarbamoyl, n-propylcarbamoyl, tert-butylcarbamoyl, etc.), $C_{3-8}$ cycloalkylcarbamoyl (e.g. cyclopentylcarbamoyl, cyclohexylcarbamoyl, etc.), $C_{6-12}$ arylcarbamoyl (e.g. phenylcarbamoyl, {4-methylphenyl}carbamoyl, etc.), $C_{7-15}$ aralkylcarbamoyl (e.g. benzylcarbamoyl, phenethylcarbamoyl, {1,2-diphenylethyl}carbamoyl, etc.), {aromatic heterocycle-$C_{1-6}$ alkyl}carbamoyl (e.g. [2-{indol-2-yl}ethyl]carbamoyl, [2-{indol-3-yl}ethyl]carbamoyl, etc.), piperidinocarbonyl, piperazinecarbonyl, $N^4$-$C_{1-6}$ alkylpiperazinecarbonyl, (e.g. $N^4$-methylpiperazinecarbonyl, $N^4$-ethylpiperazinecarbonyl, etc.), $N^4$-$C_{3-8}$ cycloalkylpiperazinecarbonyl (e.g. $N^4$-cyclopentylpiperazinecarbonyl, $N^4$-cyclohexylpiperazinecarbonyl, etc.), $N^4$-5 to 7-membered heterocycle-piperazinecarbonyl (e.g. $N^4$-pyridylpiperazinecarbonyl, $N^4$-furylpiperazinecarbonyl, $N^4$-thienylpiperazinecarbonyl, etc.), $N^4$-$C_{6-12}$ arylpiperazinecarbonyl (e.g. $N^4$-phenylpiperazinecarbonyl, $N^4$-(4-methylphenyl)piperazinecarbonyl, etc.), $N^4$-$C_{7-15}$ aralkylpiperazinecarbonyl (e.g. $N^4$-benzylpiperazinecarbonyl, $N^4$-phenethylpiperazinecarbonyl, $N^4$-{1,2-diphenylethyl}piperazinecarbonyl, etc.), $N^4$-{aromatic heterocycle-$C_{1-6}$ alkyl}piperazinecarbonyl (e.g. $N^4$-[2-{indol-2-yl}ethyl]piperazinecarbonyl, $N^4$-[2-{indol-3-yl}ethyl]piperazinecarbonyl, etc.), $N^4$-($C_{1-6}$ aliphatic acyl) piperazinecarbonyl (e.g. $N^4$-acetylpiperazinecarbonyl, $N^4$-propionylpiperazinecarbonyl, etc.), $N^4$-($C_{4-9}$ alicyclic acyl)piperazinecarbonyl (e.g. $N^4$-cyclopentanecarbonylpiperazinecarbonyl, $N^4$-cyclohexanecarbonylpiperazinecarbonyl, etc.), $N^4$-($C_{7-15}$ aryl acyl)piperazinecarbonyl (e.g. $N^4$-benzoylpiperazinecarbonyl, $N^4$-{4-methylbenzoyl}piperazinecarbonyl, etc.), $N^4$-($C_{8-16}$ aralkyl acyl)piperazinecarbonyl (e.g. $N^4$-phenylacetylpiperazinecarbonyl, $N^4$-{2-phenylpropionyl}piperazinecarbonyl, $N^4$-{3-phenylpropionyl}piperazinecarbonyl, $N^4$-diphenylacetylpiperazinecarbonyl, $N^4$-{1-naphthylacetyl}piperazinecarbonyl, $N^4$-{2-naphthylacetyl}piperazinecarbonyl, etc.), $N^4$-{aromatic heterocycle-carbonyl}piperazinecarbonyl (e.g. $N^4$-{indol-2-ylcarbonyl}piperazinecarbonyl, $N^4$-{indol-3-ylcarbonyl}piperazineamido, etc.), $N^4$-{aromatic heterocycle-alkylcarbonyl}piperazinecarbonyl (e.g. $N^4$-{indol-2-ylacetyl}piperazinecarbonyl, $N^4$-{indol-3-ylacetyl}piperazinecarbonyl, etc.), $C_{1-6}$ alkoxycarbonyl (e.g. methoxycarbonyl, ethoxycarbonyl, n-propoxycarbonyl, etc.), $C_{3-8}$ cycloalkyloxycarbonyl (e.g. cyclopentyloxycarbonyl, cyclohexyloxycarbonyl, etc.), $C_{7-15}$ aralkyloxycarbonyl (e.g. benzyloxycarbonyl, phenethyloxycarbonyl, 1-phenylethoxycarbonyl, diphenylmethoxycarbonyl, etc.), and so on. The abovementioned carbamoyl includes amides with α-amino acids and amides with oligopeptides (e.g. dipeptides, tripeptides, tetrapeptides, etc.).

The α-amino acid with substituted carboxy includes but is not limited to $N^4$-methylasparagine, $N^4$-phenylasparagine, $N^4$-benzylasparagine, $N^4$-phenethylasparagine, $N^4$-(2-{indol-3-yl}ethyl)asparagine, $N^5$-methylglutamine, $N^5$-phenylglutamine, $N^5$-benzylglutamine, $N^5$-phenethylglutamine, $N^5$-(2-{indol-3-yl}ethyl)glutamine, β-methylaspartate, β-cyclopropyl aspartate, β-benzyl aspartate, β-phenethyl aspartate, aspartic acid β-$N^4$-phenylpiperazine amide, aspartic acid β-$N^4$-(2-methylphenyl)piperazine amide, aspartic acid β-$N^4$-(3-methylphenyl)piperazine amide, aspartic acid β-$N^4$-(4-methylphenyl)piperazine amide, aspartic acid β-$N^4$-(2-methoxyphenyl)piperazine amide, aspartic acid β-$N^4$-(3-methoxyphenyl)piperazine amide, aspartic acid β-$N^4$-(4-methoxyphenyl)piperazine amide, aspartic acid β-$N^4$-(2-chlorophenyl)piperazine amide, aspartic acid β-$N^4$-(3-chlorophenyl)piperazine amide, aspartic acid β-$N^4$-(4-chlorophenyl)piperazine amide, aspartic acid β-$N^4$-(4-nitrophenyl)piperazine amide, aspartic acid β-$N^4$-(4-fluorophenyl)piperazine amide, aspartic acid β-$N^4$-(3-trifluoromethylphenyl)piperazine amide, aspartic acid β-$N^4$-(2,3-dimethylphenyl)piperazine amide, aspartic acid β-$N^4$-(2-pyridyl)piperazine amide, aspartic acid β-$N^4$-(2-pyrimidyl)piperazine amide, γ-methyl glutamate, γ-cyclopropyl glutamate, γ-benzyl glutamate, and γ-phenethyl glutamate.

Referring, further, to the formula [I], the precursor α-amino acids for the α-amino acid residues for X and Y may be whichever of D-, L-, and DL-form compounds but the L-form is preferred for both X and Y.

Y is preferably an amino acid residue selected from the precursor group consisting of aspartic acid, glutamic acid, alanine, proline, leucine and tryptophan, and more preferably an L-aspartic acid residue.

X is preferably a group of the following formula:

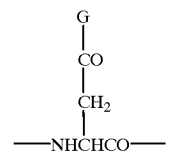

wherein G represents a group of the regional formula

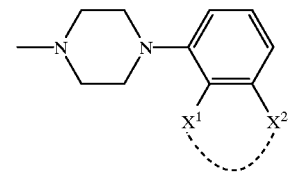

wherein $X^1$ and $X^2$ each represents hydrogen, $C_{1-6}$ alkyl, $C_{1-6}$ alkoxy, halogen or nitro;

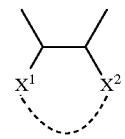

indicates that $X^1$ and $X^2$ may jointly form a ring).

The $C_{1-6}$ alkyl mentioned for $X^1$ and $X^2$ includes methyl, ethyl, n-propyl, iso-propyl, n-butyl, isobutyl, tert-butyl, n-pentyl, n-hexyl, etc. and is preferably $C_{1-3}$ alkyl, e.g. methyl, ethyl, n-propyl, and isopropyl, and more preferably methyl. The $C_{1-6}$ alkoxy mentioned for $X^1$ and $X^2$ includes methoxy, ethoxy, n-propoxy, n-butoxy, n-pentyloxy, n-hexyloxy, etc. and is preferably $C_{1-3}$ alkoxy, e.g. methoxy, ethoxy, n-propoxy, etc., and more preferably methoxy or ethoxy.

The halogen mentioned for $X^1$ and $X^2$ includes fluorine, chlorine, bromine and iodine, and is preferably chlorine.

Where $X^1$ and $X^2$ jointly form a ring, G is preferably a group of the formula

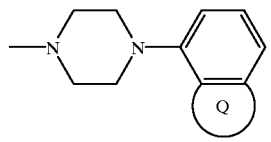

where ring Q is, for example, a 4- to 7-membered ring optionally containing 1 to 3 hetero-atoms such as O, N, and/or S (e.g. a saturated carbocycle, an aromatic carbocycle, a saturated heterocycle, or an aromatic heterocycle).

Referring to ring Q, the carbocycle includes, for example, $C_{3-8}$ cycloalkyl such as cyclopropyl, cyclobutyl, cyclopentyl, cyclohexyl, etc., $C_{3-8}$ cycloalkenyl such as cyclopropenyl, 1-cyclopentenyl, 2-cyclopentenyl, 3-cyclopentenyl, 1-cyclohexenyl, 2-cyclohexenyl, 3-cyclohexenyl, etc., and $C_{6-14}$ aryl such as phenyl, 1- or 2-naphthyl, 1-, 2- or 9-anthryl, 1-, 2-, 3-, 4- or 9-phenanthryl, 1-, 2-, 4-, 5- or 6-azulenyl, etc.

Referring to ring Q, the heterocycle includes, for example, a 5- to 8-membered ring containing 1–4 hetero-atoms selected from among oxygen, sulfur, nitrogen, etc. in addition to carbon as ring members or the corresponding fused hetero system, for example, 5-membered rings each containing 1–4 hetero-atoms selected from among oxygen, sulfur, nitrogen, etc. in addition to carbon, such as 2- or 3-thienyl, 2- or 3-furyl, 2- or 3-pyrrolyl, 2-, 4- or 5-oxazinyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,2,5-thiadiazolyl, 1,2,3-triazolyl, 1,2,4-triazolyl, 1H- or 2H-tetrazolyl, etc.; 6-membered rings each containing 1–4 hetero-atoms selected from among oxygen, sulfur, nitrogen, etc. in addition to carbon, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, oxoimidazinyl, dioxotriazinyl, pyrrolidinyl, piperazinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl, N-oxido-3- or 4-pyridazinyl, etc.; and bicyclic or tricyclic fused systems containing 1–4 hetero-atoms selected from among oxygen, sulfur, nitrogen, etc. in addition to carbon as ring members, such as benzofuryl, benzothiazolyl, benzoxazolyl, tetrazolo[1,5-b]pyridazinyl, triazolo[4,5-b]pyridazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, chromanyl, benzoxazinyl, phenazinyl, phenothiazinyl, phenoxazinyl, etc.

Among the above-mentioned examples, G is preferably a group of the formula

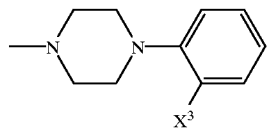

wherein $X^3$ represents hydrogen, $C_{1-6}$ alkyl, $C_{1-6}$ alkoxy, halogen or nitro. Specific examples are as follows.

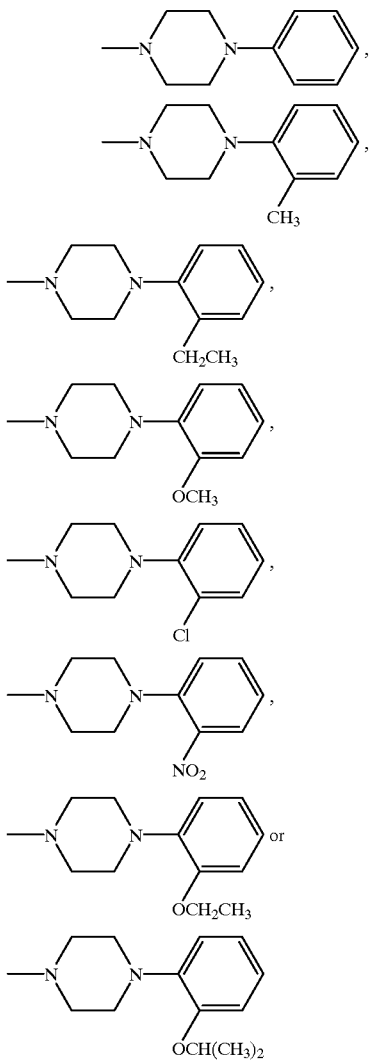

Particularly preferred is

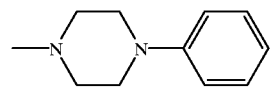

Thus, the most suitable species of X is an aspartic acid β-4-phenylpiperazine amide residue. Moreover, G includes D-, L-, and DL-forms and the L-form is particularly preferred.

The precursor amino acid for the D-acidic-α-amino acid residue represented by A in the formula [I] includes, for example, an amino acid having an acidic side-chain group such as carboxyl, sulfonyl or tetrazolyl. Among preferred examples are D-glutamic acid, D-aspartic acid, D-cysteic acid, D-homocysteic acid, D-β-(5-tetrazolyl)alanine, D-2-amino-4-(5-tetrazolyl)butyric acid, etc. Particularly, D-glutamic acid, D-aspartic acid and D-cysteic acid are preferred. The most preferred species of A is a D-aspartic acid residue.

The precursor amino acid for the neutral-α-amino acid residue represented by B in the formula [I] includes a variety of α-amino acids such as alanine, valine, norvaline, leucine, isoleucine, alloisoleucine, norleucine, tert-leucine, γ-methylleucine, phenylglycine, phenylalanine, 1-naphthylalanine, 2-naphthylalanine, proline, 4-hydroxyproline, azetidine-2-carboxylic acid, pipecolic acid (piperidine-2-carboxylic acid), 2-thienylalanine, 2-thienylglycine, 3-thienylglycine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, 1-aminocycloheptane-1-carboxylic acid, 2-cyclopentylglycine, 2-cyclohexylglycine, etc. Where the neutral-α-amino acid exists in L- and D-forms, the D-form is preferred. Particularly preferred are D-neutral-α-amino acid residues optionally having 5- or 6-membered heterocycles each containing 1–4 heteroatoms selected from among oxygen, sulfur and nitrogen, which may optionally be substituted by $C_{1-6}$ alkyl, $C_{5-7}$ cycloalkyl, $C_{7-11}$ aralkyl, $C_{6-10}$ aryl, $C_{1-6}$ alkoxy or $C_{1-6}$ alkanoyl. Still more preferred are D-leucine, D-alloisoleucine, D-tert-leucine, D-γ-methylleucine, D-phenylglycine, D-2-thienylalanine, D-2-thienylglycine, D-3-thienylglycine and D-2-cyclopentylglycine. The most preferred species of B is a D-2-thienylglycine residue. The α-amino group of such neutral-α-amino acids may be substituted by $C_{1-6}$ alkyl (e.g. methyl, ethyl, n-propyl, tert-butyl, etc.). Among such α-amino acids are N-methylleucine, N-methylalloisoleucine, N-methyl-tert-leucine, N-methyl-γ-methylleucine, and N-methylphenylglycine. As to these neutral-α-amino acids, the D-form is preferred.

B is preferably a D- or L-neutral-α-amino acid residue selected from the group consisting of a phenylglycine, phenylalanine, 1-naphthylalanine, 2-naphthylalanine, 2-thienylalanine, 2-thienylglycine, 3-thienylglycine, proline, 4-hydroxyproline, azetidine-2-carboxylic acid, piperidine-2-carboxylic acid, 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid residue which is optionally substituted by a $C_{1-6}$ alkyl, and the D-form of the neutral-α-amino acid is preferred.

The precursor amino acid for the L-α-amino acid residue represented by C in the formula [I] includes those L-α-amino acids which are generally known, such as glycine, L-alanine, L-valine, L-norvaline, L-leucine, L-isoleucine, L-tert-leucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine, L-proline, etc. Particularly preferred are L-leucine, L-norleucine and L-tryptophan. The most preferred species of C is an L-leucine residue. The α-amino acid of such L-α-amino acids may be substituted by $C_{1-6}$ alkyl (e.g. methyl, ethyl, n-propyl, tert-butyl, etc.). Among such L-α-amino acids are L-N-methylleucine, L-N-methylnorleucine and L-N(α)-methyltryptophan.

The precursor amino acid for the D-α-amino acid residue having an aromatic ring group represented by E in the formula [I] includes D-α-amino acids having an aromatic ring in side chains. Among such amino acids are D-tryptophan, D-5-methyltryptophan, D-phenylalanine, D-tyrosine, D-1-naphthylalanine, D-2-naphthylalanine, D-3-benzothienylalanine, D-4-biphenylalanine, and D-pentamethylphenylalanine. Preferred are D-tryptophan and D-5-methyltryptophan. Particularly preferred is D-tryptophan. The α-amino group of such D-α-amino acid having an aromatic ring group may be substituted by $C_{1-6}$ alkyl (e.g. methyl, ethyl, n-propyl, tert-butyl, etc.) and the indole ring amino group of D-tryptophan may be substituted by hydrocarbon group such as $C_{1-6}$ alkyl (e.g. methyl, ethyl, n-propyl, tert-butyl, etc.), $C_{3-8}$ cycloalkyl (e.g. cyclopentyl, cyclohexyl, etc.), $C_{6-12}$ aryl (e.g. phenyl, 4-methylphenyl, etc.) and $C_{7-15}$ aralkyl (e.g. benzyl, phenethyl, etc.) or acyl such as $C_{1-6}$ aliphatic acyl, preferably $C_{1-6}$ alkanoyl, (e.g. formyl, acetyl, propionyl, etc.), $C_{4-9}$ alicyclic acyl, preferably $C_{5-7}$ cycloalkylcarbonyl, (e.g. cyclopentanecarbonyl, cyclohexanecarbonyl, etc.), $C_{7-15}$ aryl acyl, preferably $C_{6-12}$ arylcarbonyl, (e.g. benzoyl, 4-methylbenzoyl, etc.), $C_{8-16}$ aralkyl acyl, preferably $C_{6-12}$ aryl-$C_{2-4}$ alkanoyl, (e.g. phenylacetyl, 2-phenylpropionyl, 3-phenylpropionyl, diphenylacetyl, etc.) and $C_{1-6}$ alkoxycarbonyl (e.g. methoxycarbonyl, ethoxycarbonyl, etc.). Among such α-amino acids are D-N(α)-methyltryptophan, D-N-methylphenylalanine, D-N-methyltyrosine, D-$N^{in}$-methyltryptophan, D-$N^{in}$-ethyltryptophan, D-$N^{in}$-formyltryptophan and D-$N^{in}$-acetyltryptophan. Among them, D-$N^{in}$-methyltryptophan, D-$N^{in}$-formyltryptophan and D-$N^{in}$-acetyltriptophan are preferred. The most preferred species of E is a D-tryptophan residue.

The preferred specific examples of the peptide of the formula [I] or its salt are as follows.

X is L-configured; Y is L-configured; A is a group selected from the class consisting of D-glutamic acid residue, D-aspartic acid residue, D-cysteic acid residue and D-tetrazolylalanine residue; B is D-configured, B is a group selected from the class consisting of 1-aminocyclopropane-1-carboxylic acid residue, 1-aminocyclobutane-1-carboxylic acid residue, 1-aminocyclopentane-1-carboxylic acid residue, 1-aminocyclohexane-1-carboxylic acid residue and 1-aminocycloheptane-1-carboxylic acid residue, and B is a group selected from the class consisting of D-leucine residue, D-alloisoleucine residue, D-tert-leucine residue, D-γ-methylleucine residue, D-phenylglycine residue, D-2-thienylglycine residue, D-3-thienylglycine residue, D-2-cyclopentylglycine residue, D-phenylalanine residue, D-2-thienylalanine residue, D-valine residue, D-2-furylglycine residue and D-3-furylglycine residue; C is a group selected from the class consisting of L-leucine residue, L-isoleucine residue, L-valine residue, L-norleucine residue and a L-α-amino acid residue having an aromatic ring group; E is a group selected from the class consisting of D-tryptophan residue, D-tryptophan derivative residue, D-1-naphthylalanine residue, D-2-naphthylalanine residue, D-benzothienylalanine residue, D-4-bisphenylalanine residue and D-pentamethylphenylalanine residue, the D-tryptophan derivative being a group selected from the class consisting of D-$N^{in}$-methyltryptophan residue, D-$N^{in}$-formyltryptophan residue and D-$N^{in}$-acetyltryptophan residue.

Still more preferred examples are as follows.

A is a D-aspartic acid residue; X is a tryptophan residue, L-(β-4-phenylpiperazineamido)aspartic acid residue, L-[β-4-(2-methoxyphenyl)piperazineamido]aspartic acid residue, L-N-(δ)-phenylacetylornithine residue, L-($N^4$-[indol-3-yl]acetyl)ornithine residue, L-(4-benzyloxy)proline residue, L-($N^5$-benzyl)glutamine residue or L-(N(δ)-[indol-3-yl]ethyl)aspartic acid residue; Y is a L-leucine residue, L-asparagine residue or L-O-benzylserine residue; B is a D-leucine residue, D-γ-methylleucine residue, D-2-thienylglycine residue or D-3-thienylglycine residue; C is a L-leucine residue, L-phenylalanine residue or L-tryptophan residue; and E is a D-tryptophan residue.

Specially preferred examples are as follows.

X is a tryptophan, L-(β-4-phenylpiperazineamido) aspartic acid, L-[β-4-(2-methoxyphenyl)piperazineamido)

aspartic acid, L-N(δ)-phenylacetylornithiene, L-(N⁴-[indol-3-yl]acetyl)ornithine, L-(4-benzyloxy)proline, L-(N⁵-benzyl)glutamine or L-(N(δ)-[indol-3-yl]ethyl)aspartic acid residue; Y is an L-aspartic acid or L-leucine residue; A is an D-aspartic acid residue; B is a D-2-thienylglycine residue; C is an L-leucine, L-phenylalanine or L-tryptophan residue; and E is a D-tryptophan residue.

The most preferred cyclic hexapeptide, ester or salt thereof is the compound of the following formula [I] or a salt thereof, and the salt is preferably the disodium salt.

Cyclo[-D-Asp-Asp(R1)-Asp-D-Thg(2)-Leu-D-Trp-]

[wherein Asp(R1) is an aspartic acid β-4-phenylpiperazine amide residue and Thg(2) is a 2-thienylglycine residue].

The ester of compound represented by the formula [I] may, for example, be an alkyl ester of the side-chain carboxyl group, if any, of an α-amino acid residue. As the alkyl group forming such an ester includes $C_{1-6}$ alkyl groups such as methyl, ethyl, n-propyl, iso-propyl, n-butyl, iso-butyl, tert-butyl, n-pentyl, n-hexyl, etc.

The cyclic hexapeptide [I] (compound of the formula [I]) for use in the present invention can be synthesized by the process described in JP-A-6-9689 and EP-A-528,312, any process analogous thereto, or the routine peptide synthesis technology.

Thus, whichever of the method of liquid-phase synthesis and the method of solid-phase synthesis can be employed, although liquid-phase synthesis is advantageous in certain cases. For such peptide synthesis, any of the known methods can be employed. For example, the methods described in M. Bodansky and M. A. Ondetti, Peptide Synthesis, Interscience New York, 1966; F. M. Finn and K. Hofmann, The Proteins, Vol. 2, H. Nenrath and R. L. Hill (ed.), Academic Press Inc., New York, 1976; Nobuo Izumiya et al., Peptide Gosei-no-Kiso-to-Jikken [The Fundamentals and Experiments of Peptide Synthesis], Maruzen, 1985; Haruaki Yajima, Shumpei Sakakibara, et al., Seikagaku Jikken Koza 1 [Biochemical Experiment Seminars 1], Japanese Biochemical Society (ed.), Tokyo Kagaku Dojin, 1977; Toshiya Kimura, Zoku Seikagaku Jikken Koza 2 [Continued Biochemical Experiment Seminars 2], Japanese Biochemical Society (ed.), Tokyo Kagaku Dojin, 1987; and J. M. Stewart and J. D. Young, Solid Phase Peptide Synthesis, Pias Chemical Company, Illinois, 1984, among other literature. Thus, any of the azide method, acid chloride method, acid anhydride method, mixed acid anhydride method, DCC method, active ester method, Woodward reagent K method, carbonylimidazole method, redox method, DCC/HONB method, and BOP reagent method, among others, can be employed.

The cyclic hexapeptide [I] for use in the present invention can be synthesized by condensing a reactive carboxyl group-containing starting compound corresponding to either one of the two fragments available on splitting the objective peptide imaginally in any desired amide bond position with a reactive amino group-containing starting compound corresponding to the other fragment by a per se known procedure, deprotecting the C-terminal a-carboxyl group and N-terminal α-amino group either concurrently or serially, and causing the two deprotected groups to undergo intramolecular condensation in the per se known manner to provide a cyclic compound, followed, if this product compound has any further protective group, by removing the protective group by a conventional procedure.

Each of the first-mentioned starting compound and the second-mentioned starting compound is usually an amino acid or a peptide, and when they are condensed together, give rise to the objective cyclic hexapeptide [I] or a salt thereof. These starting compounds are generally straight-chain or branched. The term "reactive carboxyl group" used here means either a free carboxyl group or an activated carboxyl group. The "reactive amino group" means a free amino group or an activated amino group. Usually, one of these two functional groups is activated for the condensation reaction. Any carboxyl and/or amino group that should not take part in the condensation are previously protected prior to initiation of the condensation reaction.

Protection of functional groups which should not be involved in the contemplated condensation, protective groups that can be used for such protection, removal of the protective groups, and activation of functional groups for condensation can also be selected from the public domain.

The protective group that can be used for protecting the amino group of the starting compound includes but is not limited to benzyloxycarbonyl, tert-butyloxycarbonyl, tert-amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphinothioyl and 9-fluorenylmethyloxycarbonyl.

The carboxyl group can be protected in the form of an alkyl ester (e.g. methyl, ethyl, propyl, butyl, tert-butyl, cyclopentyl, cyclohexyl, cycloheptyl, cyclooctyl and 2-adamantyl esters), benzyl ester, 4-nitrobenzyl ester, 4-methoxybenzyl ester, 4-chlorobenzyl ester, benzhydryl ester, phenacyl ester, benzyloxycarbonylhydrazide, tert-butyloxycarbonylhydrazide or tritylhydrazide for instance.

The hydroxyl group of serine can be protected by esterification or etherification. The group suitable for the esterification includes but is not limited to carboxylic acid-derived acyl groups such as lower aliphatic acyl groups such as acetyl, aryl acyl groups, such as benzoyl, benzyloxycarbonyl and ethoxycarbonyl. The group suitable for the etherification includes but is not limited to benzyl, tetrahydropyranyl and tert-butyl. However, the hydroxyl group of serine need not necessarily be protected.

The protective group for the phenolic hydroxyl group of tyrosine includes but is not limited to benzyl, 2,6-dichlorobenzyl, 2-nitrobenzyl, 2-bromobenzyloxycarbonyl and tert-butyl. However, this phenolic hydroxyl group need not necessarily be protected.

Methionine may optionally be protected in sulfoxide form.

The protective group for the imidazole ring of histidine includes but is not limited to p-toluenesulfonyl, 4-methoxy-2,3,6-trimethylbenzenesulfonyl, 2,4-dinitrophenyl, benzyloxymethyl, tert-butoxymethyl, tert-butoxycarbonyl, trityl and 9-fluorenylmethyloxycarbonyl. However, this imidazolyl group need not necessarily be protected.

The protective group for the indole ring of tryptophane includes but is not limited to formyl, 2,4,6-trimethylbenzenesulfonyl, 2,4,6-trimethoxybenzenesulfonyl, 4-methoxy-2,3,6-trimethylbenzenesulfonyl, 2,2,2-trichloroethoxycarbonyl and diphenylphosphinothioyl. However, this indole ring need not necessarily be protected.

The activated form of carboxyl of a starting compound includes the corresponding acid anhydride, azide and active ester (ester with alcohols such as pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide, N-hydroxybenzotriazole, etc.). The activated form of amino group of a starting compound includes but is not limited to the corresponding phosphoramide.

The condensation reaction can be conducted in the presence of a solvent. The solvent can be selected from among those solvents known to be of use for peptide bond-forming reactions. Thus, for example, anhydrous or hydrous N,N-dimethylformamide, dimethyl sulfoxide, pyridine, chloroform, dioxane, dichloromethane, tetrahydrofuran, acetonitrile, ethyl acetate, N-methylpyrrolidone, etc. and suitable mixtures thereof can be mentioned.

The reaction temperature is selected from the range known to be of use for peptide bond-forming reactions, generally the range of about −20° C. to about 30° C.

The intramolecular cyclization reaction can be caused to take place in a desired position of the linear peptide by a known process. A typical process comprises removing the terminal α-carboxy-protecting group from the C-terminal amino acid of the protected peptide by a known method, activating the free α-carboxyl group by a known method, removing the terminal α-amino-protecting group of the N-terminal amino acid, and allowing the peptide to cyclize intramolecularly. An alternative process comprises removing the terminal-α-carboxy-protective group of the C-terminal acid of the protected linear peptide and the terminal α-amino-protecting group of the N-terminal amino acid of the same peptide concurrently and causing the deprotected peptide to undergo ring-closing condensation by a known procedure. There are cases in which the intramolecular condensation can be more advantageously carried out in highly diluted liquid phase.

The deprotecting reaction includes but is not limited to catalytic reduction in a hydrogen stream in the presence of a catalyst such as Pd/black or Pd/carbon, treatment with an acid such as anhydrous hydrogen fluoride, methanesulfonic acid, trifluoromethanesulfonic acid, trifluoroacetic acid, or a mixture of such acids, and reduction with sodium metal in liquid ammonia.

The deprotection by acid treatment is generally carried out at a temperature of −20° C. to 40° C., and in this acid treatment, addition of a cation acceptor such as anisole, phenol, thioanisole, m-cresol, p-cresol, dimethyl sulfide, 1,4-butanedithiol, 1,2-ethanedithiol, or the like is advantageous. The 2,4-dinitrophenyl group used for protecting the imidazole ring of histidine can be removed by treatment with thiophenol and the formyl group used for protecting the indole ring of tryptophan can be removed by alkali treatment with dilute sodium hydroxide solution or dilute ammonia as well as by the acid treatment in the presence of 1,2-ethanedithiol, 1,4-butanedithiol, or the like.

The cyclic hexapeptide [I] thus produced in the reaction mixture can be recovered by the known peptide separation and purification technology such as extraction, redistribution, reprecipitation, recrystallization, column chromatography and high performance liquid chromatography.

The cyclic hexapeptide [I] for use in the present invention can be isolated in the form of a salt, e.g. salts with said metals, salts with bases or basic compounds, inorganic acid addition salts, organic acid addition salts, etc. and preferably as pharmaceutically acceptable acid addition salts, for example salts with inorganic acids (e.g. hydrochloric acid, sulfuric acid, phosphoric acid) or organic acids (e.g. acetic acid, propionic acid, citric acid, tartaric acid, malic acid, oxalic acid, methanesulfonic acid, etc.), by the per se known procedure.

When any amino acid or peptide is referred to by an abbreviation in this specification, the abbreviation recommended by IUPAC-IUB Commission on Biochemical Nomenclature or in routine use in the art is used. The following is a partial listing of such abbreviations.

| | |
|---|---|
| Gly | glycine |
| Sar | sarcosine (N-methylglycine) |
| Ala | alanine |
| Val | valine |
| Nva | norvaline |
| Ile | isoleucine |
| aIle | alloisoleucine |
| Nle | norleucine |
| Leu | leucine |
| N-MeLeu | N-methylleucine |
| tLeu | tert-leucine |
| γ MeLeu | gamma-methylleucine |
| Met | methionine |
| Arg | arginine |
| Arg(Tos) | $N^g$-p-toluenesulfonylarginine |
| Lys | lysine |
| Lys(Mtr) | $N(\epsilon)$-(4-methoxy-2,3,6-trimethyl-benzenesulfonyl)lysine |
| Orn | ornithine |
| Orn(COPh) | $N(\delta)$-benzoylornithine |
| Orn(COCH$_2$Ph) | $N(\delta)$-phenylacetylornithine |
| Orn(COCH$_2$CH$_2$Ph) | $N(\delta)$-(3-phenylpropionyl)ornithine |
| Orn(COCH$_2$-Ind) | $N(\delta)$-({indol-3-yl}acetyl)ornithine |
| His | histidine |
| His(Bom) | $N(\pi)$-benzyloxymethylhistidine |
| His(Bzl) | $N(\tau)$-benzylhistidine |
| Asp | aspartic acid |
| Asn(CH$_2$Ph) | $N^4$-benzylasparagine |
| Asn(CH$_2$CH$_2$Ph) | $N^4$-phenethylasparagine |
| Asn(CH$_2$CH$_2$-Ind) | $N^4$-(2-{indol-3-yl}ethyl)asparagine |
| Asn(Me.CH$_2$CH$_2$Ph) | $N^4$-methyl-$N^4$-phenethylasparagine |
| Asn(CH$_2$CHMePh) | $N^4$-({2-phenyl}propyl)asparagine |
| Asp(R1) | aspartic acid β-4-phenylpiperazine amide |
| Asp(R2) | aspartic acid β-4-phenylpiperidine amide |
| Asp(R3) | aspartic acid β-indoline amide |
| Asp(R4) | aspartic acid β-1-aminoindan amide |
| Asp(R5) | aspartic acid β-1-aminotetrahydronaphthalene amide |
| Asp(R6) | aspartic acid β-4-acetylpiperazine amide |
| Asp(R7) | aspartic acid β-4-(2-chlorophenyl) piperazine amide |
| Asp(R8) | aspartic acid β-4-(3-chlorophenyl)-piperazine amide |
| Asp(R9) | aspartic acid β-4-(4-chlorophenyl)piperazine amide |
| Asp(R10) | aspartic acid β-4-(2-methoxyphenyl)piperazine amide |
| Asp(R11) | aspartic acid β-4-(4-methoxyphenyl)piperazine amide |
| Asp(R12) | aspartic acid β-4-(2-ethoxyphenyl)piperazine amide |
| Asp(R13) | aspartic acid β-4-(2-fluorophenyl)piperazine amide |
| Asp(R14) | aspartic acid β-4-(4-fluorophenyl)piperazine amide |
| Asp(R15) | aspartic acid β-4-(3-trifluoro-methylphenyl)piperazine amide |
| Asp(R16) | aspartic acid β-4-(2-pyridyl)-piperazine amide |
| Glu | glutamic acid |
| Gln(CH$_2$Ph) | $N^5$-benzylglutamine |
| Gln(CH$_2$CH$_2$Ph) | $N^5$-phenethylglutamine |
| Gln(CH$_2$CH$_2$-Ind) | $N^5$-(2-{indol-3-yl}ethyl)glutamine |
| Glu(R3) | glutamic acid γ-indoline amide |
| Glu(R4) | glutamic acid γ-1-aminoindan amide |
| Glu(R5) | glutamic acid γ-1-aminotetrahydronaphthalene amide |
| Cys | cysteine |
| Cta | cysteic acid |

-continued

| | |
|---|---|
| Ser | serine |
| Ser(Bzl) | O-benzylserine |
| Thr | threonine |
| Thr(Bzl) | O-benzylthreonine |
| Pro | proline |
| Tpr | thioproline |
| Hyp | 4-hydroxyproline |
| Hyp(Bzl) | 4-benzyloxyproline |
| Azc | azetidine-2-carboxylic acid |
| Pip | pipecolic acid (piperidine-2-carboxylic acid) |
| Phe | phenylalanine |
| N-MePhe | N-methylphenylalanine |
| Tyr | tyrosine |
| Trp | tryptophan |
| mTrp | 5-methyltryptophan |
| N-MeTrp | N(α)-methyltryptophan |
| Trp(Me) | $N^{in}$-methyltryptophan |
| Trp(For) | $N^{in}$-formyltryptophan |
| Trp(Ac) | $N^{in}$-acetyltryptophan |
| Phg | phenylglycine |
| Nal(1) | 1-naphthylalanine |
| Nal(2) | 2-naphthylalanine |
| Thi | 2-thienylalanine |
| Thg(2) | 2-thienylglycine |
| Thg(3) | 3-thienylglycine |
| Acpr | 1-aminocyclopropane-1-carboxylic acid |
| Acbu | 1-aminocyclobutane-1-carboxylic acid |
| Acpe | 1-aminocyclopentane-1-carboxylic acid |
| Achx | 1-aminocyclohexane-1-carboxylic acid |
| Achp | 1-aminocycloheptane-1-carboxylic acid |
| Tic | tetrahydroisoquinoline-2-carboxylic acid |
| Cpg | cyclopentylglycine |

The protective groups and reagents which are frequently referred to in this specification are indicated by the following abbreviations.

| | |
|---|---|
| AcOEt | ethyl acetate |
| Boc | tert-butoxycarbonyl |
| Bzl | benzyl |
| BrZ | 2-bromobenzyloxycarbonyl |
| ClZ | 2-chlorobenzyloxycarbonyl |
| Tos | p-toluenesulfonyl |
| For | formyl |
| OBzl | benzyl ester |
| OPac | phenacyl ester |
| ONB | HONB ester |
| TFA | trifluoroacetic acid |
| TEA | triethylamine |
| IBCF | isobutyl chloroformate |
| DMF | N,N-dimethylformamide |
| DCC | N,N'-dicyclohexylcarbodiimide |
| DCU | N,N'-dicyclohexylurea |
| HONB | N-hydroxy-5-norbornene-2,3-dicarboximide |
| HOBt | 1-hydroxybenzotriazole |
| DCM | dichloromethane |
| THF | tetrahydrofuran |

The anti-endothelin compound for use in the present invention includes not only the compound represented by the formula [I] or an ester thereof, or a salt thereof, but also the compounds listed in the following Table 1-1 through Table 1-6.

TABLE 1-1

| Compound | Selectivity | Literature |
|---|---|---|
| [Dpr$^1$-Asp$^{15}$]ET-1 | ETA | Proc. Natl. Acad. Sci. USA, 88, 7443–7446(1991) |
| PD142893<br>Ac-D-Dip-Leu-Asp-Ile-Ile-Trp.2Na | ETA/ETB | J. Med. Chem., 35, 3301–3303(1992) |
| PD145065<br>Ac-D-Bhg-Leu-Asp-Ile-Ile-Trp.2Na | ETA/ETB | Med. Chem. res., 3, 154–162(1993) |
| IRL-1038<br>[Cys$^{11}$-Cys$^{15}$]-ET-1(11-21) | ETB | FEBS Lett., 311, 12–16(1992) |
| BQ-123<br>cyc(D-Trp-D-Asp-Pro-D-Val-Leu) | ETA | J. Med. Chem., 35, 2139–2142(1992) |
| BQ-153<br>cys(D-Sal-L-Pro-D-Val-L-Leu-D-Trp) | ETA | Life Sci., 50, 247–255(1992) |
| BQ-485<br>perhydroazepin-1-yl-L-leucyl-D-tryptophanyl-D-tryptophan | ETA | Biochem. Biophys. Res. Commun., 195, 969–975(1993) |
| BQ-788<br>Dmpc-τ-MeLeu-D-Trp(1-CO$_2$CH$_3$)-D-Nle-OH | ETB | Proc. Natl. Acad. Sci. USA, 91, 4892–4896(1994) |
| FR139317<br>(R)-2-{(S)-2-([1-{hexahydro-1H-azepinyl}carbonyl]-amino-methyl-pentamoyl)}-amino-3-(3[1-methyl-1H-indolyl])propionylamino-3-(2-pyridyl)propionic acid | ETA | J. Pharmacol. Exp. Ther., 264, 1040–1046(1993) |
| RES-7011<br>cyc(Gly-Asn-Trp-His-Gly-Thr-Ala-Pro-Asp)-Trp-Phe-Asn-Tyr-Tyr-Trp | ETB | J. Antibiotics., 47, 269–275(1994) |
| PD151242<br>(N-[(hexahydro-1-azepinyl)carbonyl])-L-Leu(1-Me)D-Trp-D-Tyr | ETA | Br. J. Pharmacol. 111, 4–6(1994) |

TABLE 1-2

| Compound | Selectivity | Literature |
|---|---|---|
| IRL2500<br>N-(3,5-dimethylbenzoyl)-N-methyl-(D)-[(4-phenyl)-phenyl]-alanyl-L-tryptophan | ETB | J. Cardiovas. Pharmacol, 26, S393–S396(1995) |
| IRL2659<br>N-(3,5-dimethylbenzoyl)-N-methyl-(D)-[4-(3-thienyl)-phenyl]-alanyl-L-tryptophan | ETB | 4th International Conference on Endothelins(ET-IV) (1995. 4, London)<br>Trends. Pharmacol. Sci., 16, 217–222(1995) |
| IRL2796<br>N-(3,5-dimethylbenzoyl)-N-methyl-(D)-[4-(5-isoxazolyl)-phenyl]-alanyl-L-tryptophan | ETB | 4th International Conference on Endothelins(ET-IV) (1995. 4, London)<br>Trends. Pharmacol. Sci., 16, 217–222(1995) |
| WS009A<br>2-acetamido-3-[[1,4,4a,5,6,6a,7,12,12a,12b-decahydro-4a,8,12a,12b-tetra-hydroxy-3-methyl-1,7,12-trioxobenz[a]anthracen-6a-yl]-thio]pro-pionic acid | ETA | J. Antibiotics., 45, 1029–1040(1992) |
| 50-235<br>27-O-caffeoyl myricerone | ETA | FEBS Lett., 305, 41–44(1992) |
| 97-139<br>27-O-3-[2-(3-carboxy-acryloylamino)-5-hydroxy-phenyl]-acryloyloxy myricerone, sodium salt | ETA | J. Pharmacol. Exp. Ther., 268, 1122–1128(1994) |

TABLE 1-3

| Compound | Selectivity | Literature |
|---|---|---|
| Asterric acid | ETA | J. Antibiotics., 45, 1684–1685 (1992) |

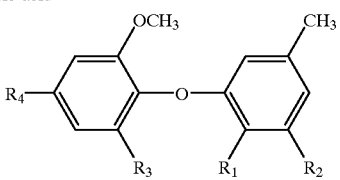

| | $R_1$ | $R_2$ | $R_3$ | $R_4$ |
|---|---|---|---|---|
| 1 | COOH | OH | COOCH$_3$ | OH |
| 2 | COOCH$_3$ | OCH$_3$ | COOCH$_3$ | OCH$_3$ |
| 3 | COOH | OH | COOH | OH |
| 4 | CONHNH$_2$ | OH | COOCH$_3$ | OH |

| Compound | Selectivity | Literature |
|---|---|---|
| Ro46-2005<br>4-tert-butyl-N-[6-(2-hydroxyethoxy)-5-(3-methoxy-phenoxy)-4-pyrimidinyl]-benzenesulphonamide | ETA/ETB | Nature, 365. 759–761 (1993) |
| Bosentan (Ro47-0203)<br>4-tert-butyl-N-[6-(2-hydroxyethoxy)-5-(2-methoxy-phenoxy)-2,2'-bipyrimidin-4-yl]-benzene sulphonamide | ETA/ETB | Circulation., 88, I-316 (1993) |
| Ro46-8443<br>4-tert-butyl-N-[(S)6-(2,3-dihydroxypropoxy)-5-(2-methoxyphenoxy)-2-(4-methoxyphenyl)-pyrimidin-4-yl]-benzene sulphonamide | ETB | J. Cardiovasc. Pharmacol, 26 (Supple. 3) S262–S264 (1995) |
| SB-209670<br>(±)-(1S,2R,3S)-3-(2-carboxy-methoxy-4-methoxy-phenyl)-1-(3,4-methylene dioxyphenyl)-5-(prop-1-yloxy)indane-2-carboxylic acid | ETA/ETB | J. Med. Chem., 37, 1553–1557 (1994) |

TABLE 1-4

| Compound | Selectivity | Literature |
|---|---|---|
| SB-217242<br>(+)-(1S,2R,3S)-3-[2-(2-hydroxyeth-1-yloxy)-4-methoxyphenyl]-1-(3,4-methylenedioxyphenyl)-5-(prop-1-yloxy)indan-2-carboxylic acid | ETA/ETB | J. Cardivas. Pharmacol., 26, S404–S407(1995) |
| BMS-182874<br>5-(dimethylamino)-N-(3,4-dimethyl-5-isoxazolyl)-1-naphthalene sulphonamide | ETA | J. Med. Chem., 37, 329–331(1994) |
| CGS-27830 | ETA/ETB | Bioorg. Med. Chem. Lett., 3, 2099–2104(1993) |

TABLE 1-4-continued

| Compound | Selectivity | Literature |
|---|---|---|
| 1,4-Dihydro-5-methoxycarbonyl-2,6-dimethyl-4-(3-nitrophenyl)-3-pyridine-carboxylic acid | | |
| PD155080 | ETA | J. Med. Chem., 38, 1259–1263(1995) |
| 2-benzo(1,3)dioxol-5-yl-3-benzyl-4-(4-methoxyphenyl)-4-oxobut-2-enoate | | |
| PD156707 | ETA | J. Pharmacol. Exp. Ther., 273, 1410–1417(1995) |
| 2-benzo(1,3)dioxol-5-yl-4-(4-methoxyphenyl)-4-oxo-3-(3,4,5-trimethoxybenzyl)-but-2-enoate | | |
| PD155719 | ETA | J. Cardiovas. Pharmacol., 26, S358–S361(1995) |
| 2-(1,3-benzodioxol-5-yl)-4-(4-methoxyphenyl)-4-oxo-3[(3-propoxyphenyl)methyl]-2-butenoic acid | | |
| PD160672 | ETA/ETB | J. Cardiovas. Pharmacol., 26, S358–S361(1995) |
| 3-benzo(1,3)dioxol-5-yl-(3,5-dimethoxy-4-pentyloxybenzyl)-5-hydroxy-5-(4-methoxyphenyl)-5H-furan-2-one | | |
| PD160874 | ETA/ETB | J. Cardiovas. Pharmacol., 26, S358–S361(1995) |
| 4-cryclohexyl-methyl-5-[2,3-dihydro-benzo(1,4)dioxin-6-yl]-5-hydroxy-3-[7-methoxybenzo(1,3)-dioxol-5-yl]-5H-furan-2-one | | |

TABLE 1-5

| Compound | Selectivity | Literature |
|---|---|---|
| L-749329 | ETA | Cur. Med. Chem., 1, 271–312(1995) |
| (±)N-(4-isopropyl benzene sulphonyl)-α-(4-carboxy-2-n-propylphenoxy)-3,4-methylene dioxyphenyl acetamide | | |
| L-751281 | ETA | 4th International Conference on Endothelins(ET-IV) (1995. 4, London) |
| (±)N-[2-(3,4-methylenedioxyphenyl)-3-(4-carbomethoxy-2-propylphenyl)-propanoly]-4-(isopropyl) benzene sulphonamide | | |
| L-754142 | ETA | JPET 275, 1518–1526(1995) |
| (−)N-(4-isopropyl benzene sulphonyl)-α-(4-carboxy-2-n-propylphenoxy)-3,4-methylene dioxyphenyl acetamide | | |
| Phosphoramidon | ECE inhibition | Eur. J. Pharmacol., 185, 103–106(1990) |
| N-phosphonyl L-Leu-L-Trp | | |
| N-2-(2-naphthyl)ethyl-phosphonyl-L-Leu-L-Trp | ECE inhibition | J. Cardiovas. Pharmacol., 26, S65–68(1995) U.S. Pat. No. 5330978 |
| CGS-26303 | ECE inhibition | Biochem. Biophys. Res. Commun., 204, 407–412(1994) |
| (S)-2-diphenyl-4-yl-1-(1H-tetrazol-5-yl)-ethyl-aminomethyl phosphonic acid | | |
| CGS-26393 | ECE inhibition | J. Cardiovas. Pharmacol., 26, S69–S71(1995) |
| diphenyl[(S)-2-diphenyl-4-yl-1-(1H-tetrazol-5-yl)-ethylamino-methyl] phosphonate | | |
| S-17162 | ECE inhibition | J. Cardiovas. Pharmacol., 26, S61–S64(1995) |
| N-(2,3 dihydroxy propyl phosphonyl)-(S)-Leu-(S)-Trp-OH, disodium salt | | |

TABLE 1-6

| Compound | Selectivity | Literature |
|---|---|---|
| Aspergillomarasmines | ECE inhibition | Jap. J. Pharmacol., 63, 187–193 (1993) |

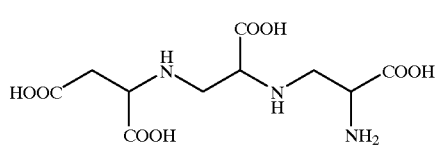

Aspergillomarasmine A(AM-A)
$C_{10}H_{17}N_3O_8$

TABLE 1-6-continued

| Compound | Selectivity Literature |
| --- | --- |
| 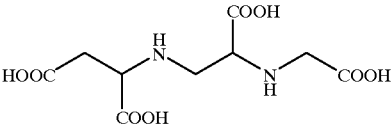<br>Aspergillomarasmine B(AM-B)<br>$C_9H_{14}N_2O_8$ | |

ETA: endothelin A receptor
ETB: endothelin B receptor
ECE: endothelin converting enzyme
ET: endothelin The compounds listed in the above Table 1-1 through Table 1-6 can be produced by known processes or in accordance with the processes disclosed in the literature cited in the tables.

The compounds listed in the above Table 1-1 through Table 1-6 and the compound of the formula [I] are classified into the category of peptide compounds [e.g. cyclic peptides such as compound of the formula [I], BQ-123, BQ-153 and RES-7011, etc. and acyclic or linear peptides such as [Dpr$^1$-Asp$^{15}$] ET-1, PD142893, PD145065, IRL-1038, BQ-485 and BQ-788, etc.] and the category of non-peptide compounds (e.g. FR139317, PD151242, and the compounds listed in Table 1-2 through Table 1-6, etc.).

For use in the present invention, peptide compounds are preferred and cyclic peptides are more preferred. Particularly preferred is the compound of the formula [I], an ester thereof, or a salt thereof.

The term "anti-endothelin activity" as used in this specification means any and all of endothelin receptor antagonistic activity (e.g. endothelin A receptor antagonistic activity, endothelin B antagonistic activity, endothelin A/endothelin B receptor antagonistic activity), endothelin converting enzyme inhibitory activity, endothelin synthase inhibitory activity, etc. Particularly preferred is endothelin receptor antagonistic activity.

The pharmaceutical composition of the present invention, which contains an anti-endothelin compound, particularly a compound of the formula [I], an ester thereof, or a salt thereof, is least toxic and is of use as a prophylactic and therapeutic drug for cerebral infarction in animals, particularly mammals (e.g. man, dog, rabbit, mouse, rat, etc.), especially obstructive cerebral infarction.

The term "cerebral infarction" is used herein to mean any and all of infarction of cerebral cortex, infarction of cerebral cortical protein, infarction of cerebral white matter, infarction of basal ganglia and internal capsule, pontine infarction, cerebellar infarction, thalamic infarction, etc. and the pharmaceutical composition of the present invention can be advantageously used especially in infarction of basal ganglia and internal capsule.

In the practice of the present invention, the anti-endothelin compound may be used in combination with other medicinally active substances effective in the prevention and treatment of infarcted brain diseases. Among such other active substances are anticoagulants (e.g. heparin, warfarin, etc.), antithrombotic agents (e.g. aspirin, dipyridamole, sulfinpyrazone, etc.), thromolytics (e.g. plasminogen activator, streptokinase, urokinase, etc.), cerebral vasodilators (e.g. cinnarizine, cyclandelate, bencyclane fumarate, etc.), peripheral vasodilators [sic. microcirculation improving agents] (e.g. low-molecular dextran, pentoxifylline, solcoseryl, etc.), and nootropic agents (e.g. citicoline, ifenprodil, etc.).

The pharmaceutical composition of the present invention which contains a compound of the formula [I] or an ester thereof, or a salt thereof, for instance, can be administered orally or non-orally. For non-oral administration, the composition can be administered by injection, by inhalation, rectally or topically, for instance. For oral administration, the composition can be used in various dosage forms such as powders, granules, tablets, pills, capsules, syrup, emulsion, elixir, suspension and solution. The unit dosage form may be the bulk powder of at least one antiendothelin compound or a mixture thereof with a pharmacologically acceptable carrier (adjuvant, excipient, binder, and/or diluent).

In the practice of the present invention, the proportion of the antiendothelin compound in the dosage form is generally 0.01–100 weight % and preferably 0.1–50 weight %.

The pharmaceutical composition can be processed into unit dosage forms by the established pharmaceutical procedures. The term "administration by injection" is used herein to mean any of subcutaneous injection, intravenous injection, intramuscular injection, intraperitoneal injection, and drip infusion, among others. An injectable dosage form such as a sterile suspension in water or oil for injection can be prepared using a suitable dispersant or wetting agent and a suspending agent in the manner well known to those skilled in the art. The sterile injectable preparation may be a sterile injectable solution or suspension in a nontoxic parenterally administrable diluent or vehicle such as aqueous medium. The vehicle that can be used includes water, Ringer's solution, and isotonic saline, among others. Moreover, sterile non-volatile oils can also be used as the solvent vehicle or suspension medium. For this purpose, a variety of nonvolatile oils and fatty acids can be used. Thus, natural, synthetic, or semisynthetic fatty oils and fatty acids and natural, synthetic, or semisynthetic mono-, di-, and triglycerides can be employed.

Suppositories for rectal administration can be manufactured by mixing the active substance with a suitable non-irritating suppository base, for example a substance which is solid at atmospheric temperature but melts at the temperature of the bowels to release the active substance, such as caccao butter and polyethylene glycol.

The solid dosage form for oral administration includes the above-mentioned dosage forms such as powders, granules, tablets, pills and capsules. Such a dosage form can be prepared by blending the active substance with at least one additive, such as sucrose, lactose, cellulose sugar, mannitol, maltitol, dextran, starch and its derivatives, agar, salts of alginic acid, chitin, chitosan, pectin, gum tragacanth, gum arabic, gelatin, collagen, casein, albumin, synthetic or semi-synthetic polymers, glycerides, etc. Such dosage forms may further contain routine additives such as an inert diluent, a lubricant such as magnesium stearate, a preservative such as parabens, sorbic acid, etc., an antioxidant such as ascorbic acid, α-tocopherol, cysteine, etc., a disintegrator, a binder, a thickener, a buffer, a sweetener, a flavorant, a perfume, etc. Tablets and pills may be enteric-coated. Liquid preparations for oral administration may typically be emulsions, syrups, elixirs, suspensions, and solutions which are medicinally acceptable and may contain any of those inert diluents, typically water, which are routinely used in the art.

The dosage for a given recipient should be selected according to, or with reference to, the recipient's age, body weight, general health status, and gender, dietary protocol, dosing schedule, planned treatment modality, excretion rate, combination of drugs, and the current severity of the disease, among other factors.

The composition containing an anti-endothelin compound, of the present invention has only a low toxicological potential and can therefore be administered safely. The daily dosage, which varies with the recipient's clinical condition and body weight, species of compound, route of administration, etc., for the composition for the prophylactic or treatment of an infarcted brain disease in an adult (60 kg) is 30–1000 mg orally, preferably 100–1000 mg orally, or 1–500 mg intravenously, preferably 3–300 mg intravenously, more preferably 30–200 mg intravenously, and this dosage is preferably administered once daily or in 2–4 divided doses.

Particularly, the pharmaceutical composition containing a compound of the formula [I] or an ester thereof, or a salt thereof, is preferably administered in a daily dosage of 3–300 mg intravenously, preferably 30–200 mg intravenously, once daily or in 2–4 divided doses.

In accordance with the present invention, anti-endothelin compounds exhibit therapeutic efficacy in cerebral infarction and are also useful for the prevention of the disease in a mammal that is a member of a population at risk thereof. Such populations include, for example, patients that have had a previous cerebral infarction.

EXAMPLES

The following examples are intended to describe the present invention in further detail and should by no means be construed as defining the scope of the invention.

Test Example 1

Effect of endothelin A and B receptor antagonist compound 1 on total cerebral infarction
Compound 1:
Cyclo[D-α-aspartyl-3-[(4-phenylpiperazin-1-yl) carbonyl]-L-aspartyl-L-α-aspartyl-D-2-(2-thienyl)glycyl-L-leucyl-D-tryptophyl] disodium salt
Method:
Mature male gerbils were divided into 2 groups and total brain infarct models were constructed by occluding the bilateral common carotid arteries for 15 minutes (Nagisa et al., Basic Pharmacology & Therapeutics, 23, 103–108, 1995). Control saline (vehicle) (group A) and compound 1 (3 mg/kg) (group B) were administered subcutaneously twice, viz. 60 minutes before obstruction and 60 minutes after reperfusion, and the survival rates at 8 hours after reperfusion were compared between the groups. In addition, the brain tissue endothelin concentration was determined by enzyme immunoassay at 5 hours following the 15-minute obstruction of the bilateral common carotid arteries. Intergroup comparison was made by ANOVA test (one-way analysis of variance).
Result:
The survival rate at 8 hours after reperfusion was 0% in group A (n=10) vs. 80% in group B (n=10). Thus, a statistically significant improvement in survival rate was obtained in group B (p<0.01).

As to the brain tissue concentration of endothelin, whereas it was 60.0±3.6 pg/g wet tissue for gerbils with no ischemia (n=6), the value was 103.2±6.3 pg/g wet tissue for gerbils at 5 hours after 15-minute obstruction of bilateral common carotid arteries (n=7), showing a statistically significant elevation (p<0.01).

These results indicate that the brain tissue endothelin concentration is increased in total cerebral infarction and that compound 1 improves the survival rate following total brain infarct.

Test Example 2

Effect of endothelin A and B receptor antagonist compound 2 on total cerebral infarction Compound 2:
4-Tert-butyl-N-[6-(2-hydroxyethoxy)-5-(2-methoxyphenoxy)-2,2'-bipyrimidin-4-yl]-benzene sulfonamide
Method:
Mature male gerbils were divided into 2 groups and total brain infarct models were constructed by obstructing the bilateral common carotid arteries for 15 minutes (Nagisa et al., Basic Pharmacology & Therapeutics, 23, 103–108, 1995). Control saline (vehicle) (Group A) and compound 2 (3 mg/kg) (Group B) were administered intraperitoneally twice, namely 60 minutes before obstruction and 90 minutes after reperfusion and the survival rates at 8 hours following reperfusion were compared between the groups. Intergroup comparison was made by ANOVA test (one-way analysis of variance).
Result:
The survival rate at 8 hours after reperfusion was 0% in group A (n=10) vs. 36% in group B (n=11). Thus, a statistically significant improvement in survival rate was obtained in group B (p<0.05).

The above results indicate that compound 2 improves the survival rate following total brain infarct.

Test Example 3

Effect of endothelin A and B receptor antagonist compound 1 on regional cerebral infarction
Method:
Male 9-week-old Wistar rats were divided into 2 groups, and regional brain infart models were constructed by modifying the middle cerebral artery obtulator obstruction-reperfusion model of Koizumi et al. (Koizumi et al., Cerebral Apoplexy, 8, 1–8, 1986). Thus, an obtulator was inserted from the left external carotid artery to occlude the middle cerebral artery at its origin and, at the same time, the bilateral common carotid arteries were obstructed with aneurismal clips. The obtulator and clips were removed 30 minutes after obstruction to establish recirculation. Immediately after reperfusion, 5 hours thereafter, twice daily on the following 2 days, and once after 3 days, or for a total of 7 times, control saline (vehicle) (group A) (n=17) and compound 1 (3 mg/kg) (group B) (n=16) were administered intravenously. Three days after reperfusion, the animals were sacrificed by decapitation and the brain was enucleated and sliced into 7 sections, 2 mm thick each. Using the brain sections stained with 2,3,5-triphenyltetrazolium hydrochloride, the infarct area was measured with an image analyzer. The infarct area of each section was expressed in percentage of the area of the ischemic hemisphere of the section. The infarct volume was expressed in the percentage of the sum of infarct areas of sections relative to the sum of areas of ischemic hemispheres for each individual. Intergroup comparison was made by ANOVA test (one-way analysis of variance).

Result:

The fractional brain infarct area of each section at 3 days after reperfusion in each of groups A and B is shown below. A statistically significant diminution of brain infarct was found in section No. 3 corresponding to the region perfused by the middle cerebral artery (p=0.039).

| Section No. | Group A | Group B |
| --- | --- | --- |
| 1 | 29.13 ± 6.70 | 23.76 ± 7.70 (p = 0.606) |
| 2 | 37.50 ± 3.82 | 24.78 ± 6.20 (p = 0.063) |
| 3 | 44.93 ± 3.69 | 33.08 ± 5.41 (p = 0.039) |
| 4 | 41.87 ± 3.11 | 31.62 ± 5.06 (p = 0.061) |
| 5 | 8.97 ± 1.90 | 6.77 ± 1.96 (p = 0.382) |
| 6 | 1.67 ± 0.64 | 1.33 ± 0.88 (p = 0.611) |
| 7 | 0.00 ± 0.00 | 0.00 ± 0.00 |

(unit: %; mean ± SE)

In addition, the fractional total brain infarct volume was 22.14±2.08% in group A vs 13.84±2.13% in group B. Thus, a tendency toward diminution of infarct was found in group B (p=0.071).

The above result indicates that, in regional brain infarction, compound 1 reduces the affected area to protect neurons.

Based on the foregoing results, it is clear that the composition of the present invention, which contains an endothelin antagonist compound, particularly an endothelin A and B receptor antagonist compound, is efficacious in cerebral infarction.

Formulation Examples

The composition containing an anti-endothelin compound for the prophylaxis or treatment of cerebral infarction according to the present invention can be prepared and provided according to the following and other formulas. In the following description, compound 1 means the same compound 1 as used in the above test examples.

| 1. Capsules | | |
| --- | --- | --- |
| (1) | Compound 1 | 10 mg |
| (2) | Lactose | 90 mg |
| (3) | Microcrystalline cellulose | 70 mg |
| (4) | Magnesium stearate | 10 mg |
| | (In each capsule) | 180 mg |

(1), (2) and (3) as well as ½ of (4) are mixed and granulated. To the granulation is added the remainder of (4) and the whole mixture is sealed in a gelatin capsule shell.

| 2. Tablets | | |
| --- | --- | --- |
| (1) | Compound 1 | 10 mg |
| (2) | Lactose | 35 mg |
| (3) | Corn starch | 150 mg |
| (4) | Microcrystalline cellulose | 30 mg |
| (5) | Magnesium stearate | 5 mg |
| | (In each tablet) | 230 mg |

(1), (2), (3), ⅔ of (4) and ½ of (5) are mixed and granulated. To the granulation are added the remainders of (4) and (5) and the whole mixture is compressed to provide a tablet.

| 3. Injection | | |
| --- | --- | --- |
| (1) | Compound 1 | 10 mg |
| (2) | Inositol | 100 mg |
| (3) | Benzyl alcohol | 20 mg |
| | (In each ampule) | 130 mg |

(1), (2) and (3) are dissolved in distilled water for injection to make 2 ml and sealed in an ampule. The sterile procedure is used throughout. 4. Injection Composition: A lyophilized product containing 5 mg, 10 mg, 25 mg, 50 mg, or 100 mg of compound 1 per vial (for extemporaneous reconstitution in saline)

Process: (1) (5 mg)

In 49 L of water for injection was dissolved 122.5 g of compound 1, and the solution was sterilized by filtration through a bacterial filter (Milli Disk). Avoiding microbial contamination in a clean room, the sterilized solution was distributed in 2 ml portions into vials and after the rubber stopper was sunken part-way, the vials were transferred to a freeze-dryer, where they were lyophilized in the routine manner. After 40 hours, dry air was introduced into the freeze-dryer to reestablish the atmospheric pressure and the stopper was sunken tight. The vial was then clinched with a plastic flip-off cap to provide a finished product.

(2) (10 mg)

Using 245 g of compound 1 and 49 L of water for injection, the procedure (1) was repeated to provide a finished product.

(3) (25 mg)

Using 612.5 g of compound 1 and 49 L of water for injection, the procedure (1) was repeated to provide a finished product.

(4) (50 mg)

Using 190 g of compound 1 and 7.6 L of water for injection, the procedure (1) was repeated to provide a finished product.

(5) (100 mg)

Using 361 g of compound 1 and 7.22 L of water for injection, the procedure (1) was repeated to provide a finished product.

We claim:

1. A method for the treatment of cerebral infarction of a mammal in need thereof which comprises administering to such mammal an effective amount of a cyclic hexapeptide of the formula:

Cyclo[-D-Asp-Asp(R1)-Asp-D-Thg(2)-Leu-D-Trp-] disodium salt wherein Asp(R1) is an aspartic acid [β-4-phenylpiperadine] β-4-phenylpiperazine amide residue, and Thg(2) is a 2-(2- thienyl)glycine residue, with a pharmaceutically acceptable excipient, carrier or diluent.

2. The method according to claim 1, wherein the cyclic hexapeptide is administered intravenously in a daily dosage of 0.5–3.3 mg/kg.

3. The method according to claim 1, wherein the cyclic hexapeptide is administered intravenously in a daily dosage of 0.5–3.3 mg/kg divided into 2–4 individual doses.

* * * * *